US00PP25554P3

(12) United States Plant Patent
Larsen

(10) Patent No.: US PP25,554 P3
(45) Date of Patent: May 12, 2015

(54) ***OSTEOSPERMUM* PLANT NAMED 'SUNOST1204'**

(50) Latin Name: *Osteospermum ecklonis*
Varietal Denomination: Sunost1204

(71) Applicant: Bjarne Nyholm Larsen, Odense (DK)

(72) Inventor: Bjarne Nyholm Larsen, Odense (DK)

(73) Assignee: Sunny Grönnegyden APS, Odense (DK)

( * ) Notice: Subject to any disclaimer, the term of this patent is extended or adjusted under 35 U.S.C. 154(b) by 141 days.

(21) Appl. No.: 13/986,420

(22) Filed: Apr. 30, 2013

(65) Prior Publication Data

US 2013/0247264 P1 Sep. 19, 2013

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — Susan McCormick Ewoldt
(74) *Attorney, Agent, or Firm* — C. A. Whealy

(57) ABSTRACT

A new and distinct cultivar of *Osteospermum* plant named 'Sunost1204', characterized by its upright, outwardly spreading and mounding plant habit; freely branching growth habit; freely flowering habit; large daisy-type inflorescences with bright golden orange-colored ray florets and dark burgundy to brown-colored disc florets; and good garden performance.

1 Drawing Sheet

Botanical designation: *Osteospermum ecklonis.*

Cultivar denomination: 'SUNOST1204'.

BACKGROUND OF THE INVENTION

The present invention relates to a new and distinct cultivar of *Osteospermum* plant, botanically known as *Osteospermum ecklonis* and hereinafter referred to by the name 'Sunost1204'.

The new *Osteospermum* plant is a product of a planned breeding program conducted by the Inventor in Odense, Denmark. The objective of the program is to create and develop new *Osteospermum* plants with compact and uniformly mounded plant habit, freely flowering habit and attractive ray and disc floret coloration.

The new *Osteospermum* plant originated from a cross-pollination by the Inventor in May, 2007 of a proprietary selection of *Osteospermum ecklonis* identified as code number 07.70.037, not patented, as the female, or seed, parent with *Osteospermum ecklonis* 'Sunost0803', not patented, as the male, or pollen, parent. The new *Osteospermum* plant was discovered and selected by the Inventor as a single flowering plant within the progeny of the stated cross-pollination in a controlled greenhouse environment in Odense, Denmark in May, 2009.

Asexual reproduction of the new *Osteospermum* plant by terminal cuttings in a controlled greenhouse environment in Odense, Denmark since November, 2011 has shown that the unique features of this new *Osteospermum* plant are stable and reproduced true to type in successive generations.

SUMMARY OF THE INVENTION

Plants of the new *Osteospermum* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunost1204'. These characteristics in combination distinguish 'Sunost1204' as a new and distinct *Osteospermum* plant:

1. Upright, outwardly spreading and mounding plant habit.
2. Freely branching growth habit.
3. Freely flowering habit.
4. Large daisy-type inflorescences with bright golden orange-colored ray florets and dark burgundy to brown-colored disc florets.
5. Good garden performance.

Plants of the new *Osteospermum* differ primarily from plants of the female parent selection in the following characteristics:

1. Plants of the new *Osteospermum* have darker green-colored leaves than plants of the female parent selection.
2. Plants of the new *Osteospermum* and the female parent selection differ in ray floret color.

Plants of the new *Osteospermum* differ primarily from plants of the male parent, 'Sunost0803', in the following characteristics:

1. Plants of the new *Osteospermum* have darker green-colored leaves than plants of 'Sunost0803'.
2. Plants of the new *Osteospermum* and 'Sunost0803' differ in ray floret color.

Plants of the new *Osteospermum* can be compared to plants of the *Osteospermum* 'Sunny Dark Florence', disclosed in U.S. Plant Pat. No. 18,606. In side-by-side comparisons conducted in Odense, Denmark, plants of the new *Osteospermum* differed from plants of 'Sunny Dark Florence' in the following characteristics:

1. Plants of the new *Osteospermum* were more vigorous than plants of 'Sunny Dark Florence'.
2. Plants of the new *Osteospermum* had larger leaves than plants of 'Sunny Dark Florence'.

3. Plants of the new *Osteospermum* had shorter and stronger peduncles than plants of 'Sunny Dark Florence'.

BRIEF DESCRIPTION OF THE PHOTOGRAPHS

The accompanying photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

The photograph at the bottom of the sheet comprises a side perspective view of a typical flowering plant of 'Sunost1204' grown in a container.

The photograph at the top of the sheet is a close-up view of a typical flowering plant of 'Sunost1204'.

DETAILED BOTANICAL DESCRIPTION

The aforementioned photographs, following observations and measurements describe plants grown during the winter and early spring in one-gallon containers in an outdoor nursery in Bonsall, Calif. and under cultural practices which approximate those generally used in commercial *Osteospermum* production. During the production of the plants, day temperatures ranged from 10° C. to 24° C., night temperatures ranged from 4° C. to 14° C. and light levels ranged from 3,500 to 5,500 foot-candles. Plants were pinched one time and were six months old when the photographs and description were taken. In the following description, color references are made to The Royal Horticultural Society Colour Chart, 2007 Edition, except where general terms of ordinary dictionary significance are used.

Botanical classification: *Osteospermum ecklonis* 'Sunost1204'.

Parentage:

*Female, or seed, parent*.—Proprietary selection of *Osteospermum ecklonis* identified as code number 07.70.037, not patented.

*Male, or pollen, parent*.—*Osteospermum ecklonis* 'Sunost0803', not patented.

Propagation:

*Type*.—Terminal vegetative cuttings.

*Time to initiate roots, summer*.—About 12 days at 18° C.

*Time to initiate roots, winter*.—About 14 days at 18° C. to 20° C.

*Time to produce a rooted cutting, summer*.—About 20 days at 18° C. to 20° C.

*Time to produce a rooted cutting, winter*.—About 28 days at 18° C.

*Root description*.—Medium in thickness, fibrous; white in color.

*Rooting habit*.—Freely branching; medium density.

Plant description:

*Plant and growth habit*.—Upright, outwardly spreading and mounding plant habit; inflorescences positioned above and beyond the foliar plane on strong peduncles; vigorous growth habit.

*Plant height*.—About 37 cm.

*Plant diameter*.—About 43 cm.

*Lateral branches*.—Quantity per plant: Freely branching habit with about 16 primary lateral branches per plant; pinching enhances branching potential. Length: About 30 cm. Diameter, primary lateral branches: About 1 cm. Diameter, secondary lateral branches: About 5 mm to 6 mm. Internode length: About 1.8 cm. Strength: Strong. Texture: Smooth, scattered hairs on older stems. Color, developing: Close to 146A. Color, mature: Close to 199A to 199B.

*Foliage description*.—Arrangement: Alternate, simple. Length: About 6.6 cm. Width: About 2 cm. Shape: Elongated spatulate. Apex: Acute. Base: Attenuate. Margin: Broadly dentate; irregular. Texture, upper surface: Smooth, glabrous. Texture, lower surface: Scattered hairs, mostly marginal. Venation pattern: Pinnate, arcuate. Color: Developing leaves, upper surface: Close to 146B to 146C. Developing leaves, lower surface: Close to 146C. Fully expanded leaves, upper surface: Close to N137B; venation, close to 147B. Fully expanded leaves, lower surface: Close to 147B; venation, close to 147C. Petiole: Length: About 1.1 cm; variable. Diameter: About 4 mm. Texture, upper surface: Smooth, glabrous. Texture, lower surface: Pubescent, minute. Color, upper surface: Close to 148C. Color, lower surface: Close to 146B.

Inflorescence description:

*Appearance*.—Daisy-type inflorescence form with ligulate-shaped ray florets; inflorescences terminal and axillary and positioned above and beyond the foliar plane on strong peduncles; disc and ray florets developing acropetally on a capitulum; inflorescences face mostly upright to slightly outwardly.

*Flowering habit*.—Freely flowering habit with about 70 inflorescences developing per plant.

*Fragrance*.—None detected.

*Flowering response*.—In southern California, plants of the new *Osteospermum* flower continuously from early spring to mid-summer; early flowering habit, plants begin flowering about two months after planting.

*Inflorescence longevity*.—Inflorescences of plants of the new *Osteospermum* last about two to three days on the plant; inflorescences persistent.

*Inflorescence buds*.—Height: About 2.3 cm. Diameter: About 1.1 cm. Shape: Lanceolate. Color: Close to 200D.

*Inflorescence size*.—Diameter: About 6.4 cm. Depth (height): About 3.5 cm. Disc diameter: About 1.1 cm. Receptacle diameter: About 1.5 cm. Receptacle height: About 1 cm.

*Ray florets*.—Length: About 3.5 cm. Width: About 7 mm. Shape: Ligulate. Apex: Emarginate. Base: Attenuate. Margin: Entire. Aspect: About 35° to 55° from peduncle axis; reflexing with development. Texture, upper and lower surfaces: Smooth, glabrous; velvety. Number of ray florets per inflorescence: About 21 arranged in 1 to 1.5 whorls. Color: When opening, upper surface: Close to N163C. When opening, lower surface: Close to 178B. Fully opened, upper surface: Close to 24B; towards the margins and apex, close to 24A; color shifting slightly to close to 26B with development. Fully opened, lower surface: Close to N163B to N163C; longitudinal striations, close to 176B to 176C; colors becoming closer to 26B and N167B, respectively, with development.

*Disc florets*.—Shape: Tubular; apex dentate, five-pointed. Length: About 9 mm. Diameter, apex: About 2 mm. Diameter, base: About 1 mm. Number of disc florets per inflorescence: About 66. Color, immature: Apex: Close to 187A. Mid-section: Close to 195A.

Base: Close to 196D. Color, mature: Apex: Close to 187A. Mid-section: Close to 199D. Base: Close to 196D.

*Phyllaries*.—Quantity per inflorescence: About 20 arranged in a single whorl. Length: About 1 cm. Width: About 1.5 mm. Shape: Lanceolate. Apex: Acuminate. Base: Truncate. Margin: Entire. Texture, upper surface: Smooth, glabrous. Texture, lower surface: Pubescent, minute. Color, upper surface: Close to 146B. Color, lower surface: Close to 146A.

*Peduncles*.—Length, terminal peduncle: About 15 cm. Length, second peduncle: About 11.5 cm. Diameter: About 1.5 mm. Strength: Strong. Aspect, terminal peduncles: Mostly upright to outwardly. Aspect, axillary peduncles: About 35° to 45° from stem axis. Texture: Scattered pubescent. Color: Close to 146C.

*Reproductive organs*.—Androecium: Present on disc florets only. Filament length: About 2.5 mm. Filament color: Close to 196D. Anther shape: Lanceolate. Anther length: About 2 mm. Anther color: Close to 200A. Pollen amount: Moderate. Pollen color: Close to N163C. Gynoecium: Present on both ray and disc florets. Pistil length: About 6 mm. Stigma shape: Biparted. Stigma color: Close to 187A. Style length: About 4 mm. Style color: Close to 158D. Ovary color: Close to 194C.

*Seeds and fruits*.—Seed and fruit development has not been observed on plants of the new *Osteospermum*.

Disease & pest resistance: Plants of the new *Osteospermum* have not been shown to be resistant to pathogens and pests common to *Osteospermum* plants.

Garden performance: Plants of the new *Osteospermum* have been observed to have good garden performance and to tolerate rain, wind, temperatures ranging from about 1° C. to about 40° C.

It is claimed:

1. A new and distinct *Osteospermum* plant named 'Sunost1204' as illustrated and described.

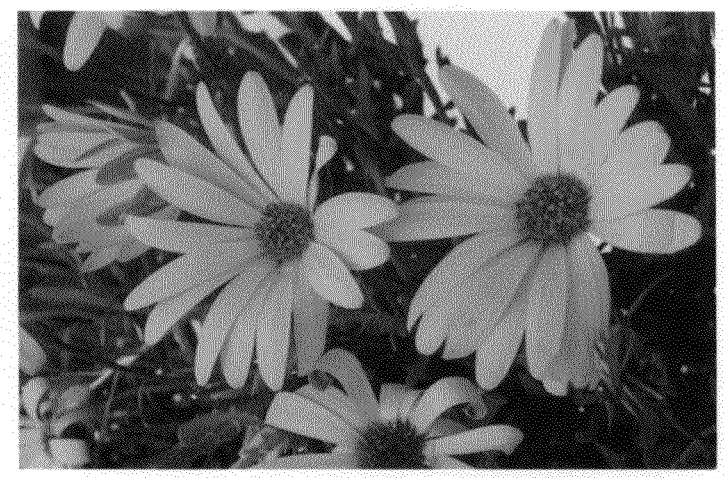
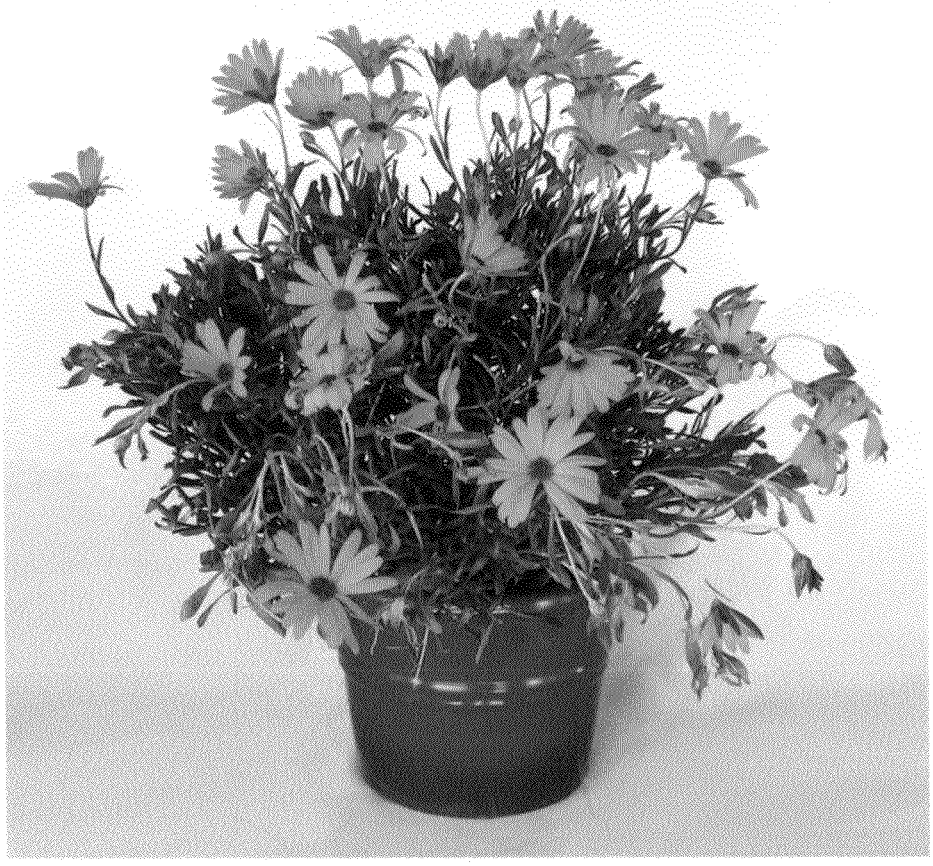

* * * * *